US006966875B1

(12) United States Patent
Longobardi

(10) Patent No.: US 6,966,875 B1
(45) Date of Patent: Nov. 22, 2005

(54) ADJUSTABLE GASTRIC IMPLANT

(75) Inventor: Bruno Longobardi, Villeurbanne (FR)

(73) Assignee: Medical Innovation Developpement, Villeurbanne (FR)

( * ) Notice: Subject to any disclaimer, the term of this patent is extended or adjusted under 35 U.S.C. 154(b) by 559 days.

(21) Appl. No.: 10/088,528

(22) PCT Filed: Sep. 29, 2000

(86) PCT No.: PCT/FR00/02706

§ 371 (c)(1),
(2), (4) Date: Apr. 24, 2002

(87) PCT Pub. No.: WO01/24742

PCT Pub. Date: Apr. 12, 2001

(30) Foreign Application Priority Data

Oct. 1, 1999 (FR) .................................. 99 12529

(51) Int. Cl.⁷ ............................................... A61F 2/02
(52) U.S. Cl. ................ 600/31; 604/96.01; 604/103.07; 606/157
(58) Field of Search ................................ 128/899, 887, 128/99.1–111.1, 118.1, 836, 846, 869; 606/151–157, 606/1, 139–158, 190–199; 604/96.01–104; 623/11.11; 600/593, 29–31

(56) References Cited

U.S. PATENT DOCUMENTS

| 5,074,868 A | | 12/1991 | Kuzmak | |
|---|---|---|---|---|
| 6,067,991 A | * | 5/2000 | Forsell | 128/899 |
| 6,676,674 B1 | * | 1/2004 | Dudai | 606/151 |

FOREIGN PATENT DOCUMENTS

| DE | 197 51 733 | | 12/1998 | |
|---|---|---|---|---|
| EP | 0876808 | * | 11/1998 | 606/151 |
| EP | 1205148 | * | 5/2002 | 606/151 |
| EP | 1319371 | * | 6/2003 | 606/151 |
| WO | 94 27504 | | 12/1994 | |

* cited by examiner

Primary Examiner—Glenn K. Dawson
(74) Attorney, Agent, or Firm—Dennison, Schultz, Dougherty & MacDonald

(57) ABSTRACT

A gastric band implant characterized in that a strap constituted by an elongate piece is secured to the inside of an inflatable bag. The width and thickness of the piece are smaller than the corresponding dimensions of an oblong right cross-section of the bag. The piece possesses convex longitudinal edges and has complementary overlapping connection structures on opposite end portions of the strap.

8 Claims, 3 Drawing Sheets

ADJUSTABLE GASTRIC IMPLANT

FIELD OF THE INVENTION

The invention relates to the field of gastric implants which are fitted around the patient's stomach so as to define a pocket or cavity of relatively small volume in the upper portion thereof which communicates with the remainder of the stomach via a channel or duct which is calibrated by means of the implant.

This field corresponds to a method of combating obesity and has been the subject of various technical proposals seeking to achieve local constriction that reduces the stomach's ability to absorb food by surgery acting locally on the stomach.

DESCRIPTION OF RELATED ART

Amongst known techniques, it is appropriate to mention the "by-pass" technique which consists in isolating an upper portion of the stomach by means of staples or the like and in connecting this portion to the outlet of the stomach via a by-pass. That technique is referred to by the term "gastric by-pass".

In reality, that method constitutes major surgery and can be considered as being irreversible, without its results in terms of weight control being found to be fully satisfactory.

Another method proposed in the prior art, known as "vertical gastroplasty", is calibrated by means of a resilient band.

Such a method implies defining a channel of small section from the zone where the esophagus and the stomach join by using several rows of staples with an open resilient band at the base of said channel achieving a constriction effect thereon.

That kind of surgery gives rise to frequent secondary complications involving a high rate of further surgery, even though statistics show that food tolerance is mediocre.

A third technique consists in placing an adjustable gastric strap in a high, sub-hiatal position, the strap including a variable-volume cavity engaging the outside wall of the stomach and capable of being filled with a liquid by means of a control box implanted under the skin.

That technique is known as "adjustable gastric banding" and can be considered as providing the best results available at present, for various reasons.

The first is that the surgery can be performed using a celioscope or laparoscope making it possible to benefit from operating conditions that are satisfactory and non-traumatizing. The second is the ease with which the stomach constriction effect can be adjusted by filling the liquid-filled cavity.

To implement such a technique, various proposals have been put forward, and amongst those proposals reference can be made to the teaching of application EP 0 769 282 which relates to a device for reducing a patient's nourishment, which device comprises a flexible but non-stretchable strap of relatively narrow width having a tubular bag of stretchable flexible material secured to one of its faces, generally by adhesive.

The bag is connected by a tube to a box provided with a self-sealing membrane which can be pierced by a syringe needle or the like, thereby enabling a liquid such as physiological serum to be injected or removed so as to control the extent to which the bag is inflated for the purpose of inducing a stomach-constricting effect.

End portions are provided at the ends of the device so as to make it possible to close the strap in the form of a closed loop by connecting its end portions together, thus enabling the bag to contribute to forming the inner peripheral surface of the band.

It can be considered that such a device makes it possible to satisfy the object of localized implantation and constriction of the stomach, but experience has shown up various drawbacks relating to such a device.

Firstly, its end portions for enabling the strap to be closed as a loop are not suitable for providing a band of regular shape approximating closely to an ideal circular section. This gives rise to spot concentrations of stresses that subject the stomach wall to localized pressures which can give rise to intolerance phenomena, and even in some cases can be responsible for local puncturing. In addition, the existence of a constriction band of internal section that is not regular is also unfavorable for defining a small-section passage suitable for establishing basically satisfactory transit.

It has also been found, in particular because of its method of manufacture, that an elongate strap that is flexible but not stretchable possesses edges running along its longitudinal sides which are sharp and consequently liable to injure the stomach wall.

It has even been found that these sharp edges can give rise to local puncturing which naturally requires corrective surgery to be performed very quickly.

It has also been found that, because of the sharp edges, connecting the strap and the bag together by means of adhesive can also lead to a risk of the inflated bag being punctured, thus preventing the bag from calibrating the channel and also being responsible for effusion of the inflation liquid, even though this liquid is generally of a physiological kind.

Finally, it should be observed that the nature of the means for interconnecting the end portions cause these means, once they have been connected together, to take up a diverging configuration like the open blades of a pair of scissors, and in this state, said end portions are then often responsible for damaging, irritating, or indeed puncturing the stomach wall.

An object of the present invention is to improve gastric implants of the above type, such improvements together overcoming the drawbacks attached to solutions or embodiments that make use of a strap that is prefabricated separately from a bag and that is connected to the bag by any appropriate means, such as adhesive in particular, as described above.

SUMMARY OF THE INVENTION

To achieve the above objects, the gastric implant of the invention is of the type comprising a strap of flexible but non-stretchable material associated with a tubular bag of deformable flexible material, the bag being closed at one end and communicating at its other end with a tube connected to a box including a self-sealing membrane that can be pierced by a needle for injecting and/or removing a fluid to control at will the extent to which the bag is filled, said strap being provided at its ends with complementary end portions enabling the strap to be looped to form a band whose inner peripheral surface is occupied by the bag, said implant being characterized in that:

the strap is constituted by an elongate piece secured to the inside of the bag and of a width and a thickness that are smaller than the corresponding dimensions of the oblong right cross-section of the bag;

the piece possesses convex longitudinal edges; and complementary overlapping connection means are provided between the end portions of the piece, which means project outside the bag.

Various other characteristics appear from the following description given with reference to the accompanying drawings which show embodiments and implementations of the invention as non-limiting examples.

DESCRIPTION OF THE PREFERRED EMBODIMENTS

Figure 1:
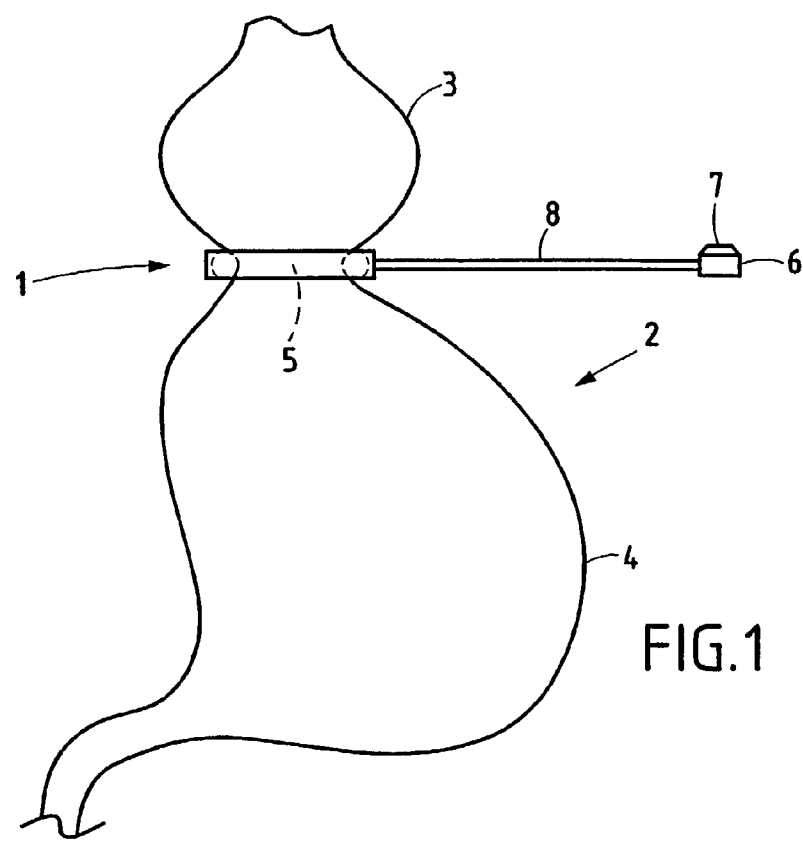
FIG. 1 is a diagram showing how the gastric band of the invention is applied.

FIG. 1 is a diagram showing how a gastric band given reference 1 is implanted in a high, sub-hiatal position on a stomach 2 so as to define an artificial top gastric pocket 3 which is in communication with a bottom gastric pocket 4 via a communicating channel 5 of through section controlled by the gastric implant 1.

Figure 2:
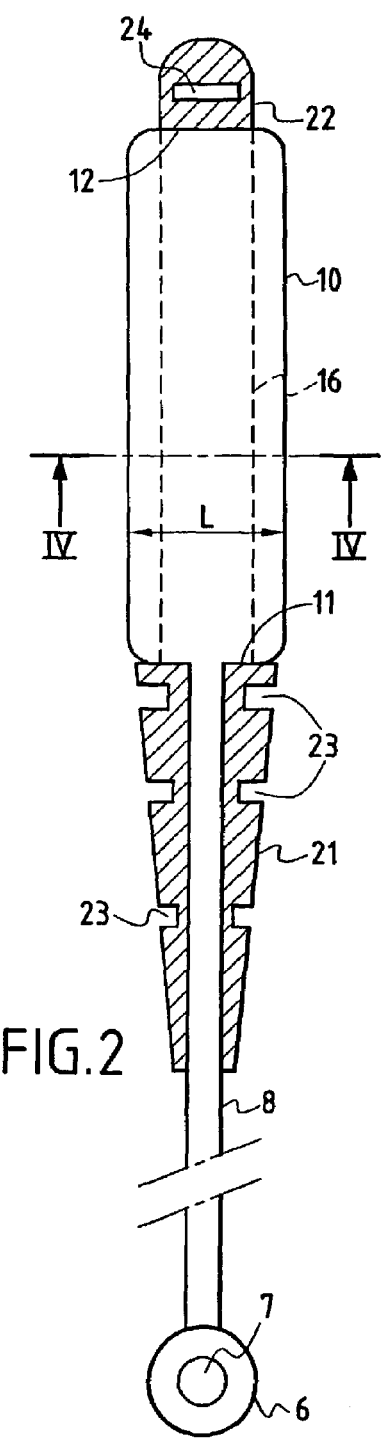
FIG. 2 is a developed plan view of the gastric implant of the invention.
Figure 3:
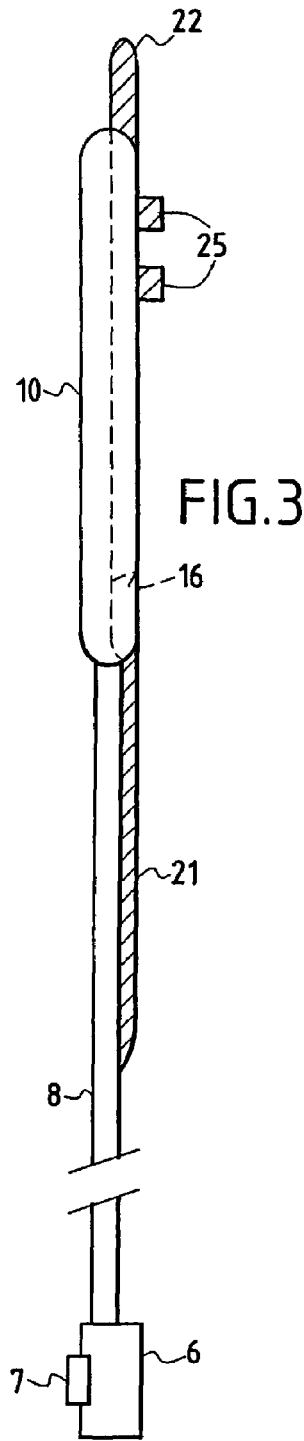
FIG. 3 is a side elevation view on line III—III of FIG. 2.

In a known disposition, the gastric implant 1 is constituted in the form of a closed-loop belt or hoop for generating constriction in the stomach wall by means of a bag that is inflatable with liquid, such as physiological serum, that is taken from or inserted into said bag by means of a box 6 possessing a self-sealing membrane 7 which can be pierced by means of the needle of a suitable syringe, or by analogous means. The box 6 is connected to the inflatable bag via a flexible tube 8 of length and flexibility selected to facilitate implantation of the box 6 under the skin. In accordance with the invention, the gastric implant 1 is characterized by a structure of the kind shown in FIGS. 2 to 4 for the function and use described above.

BEST MANNER OF PERFORMING THE INVENTION

In these figures, the gastric implant 1 comprises a bag 10 of generally tubular shape that is made of a suitable flexible material that is elastically deformable. Selecting this material forms part of the competence of the person skilled in the art.

A first end 11 of the tubular bag 10 is connected to the tube 8, and the bag is closed at its second end 12.

The tubular bag 10 is made in such a manner as to present a right cross-section that is oblong, being defined by two plane sides 13 and 14 which are interconnected by two convex edges 15 occupying the longitudinal edges of the bag between its ends 11 and 12.

Figure 4:
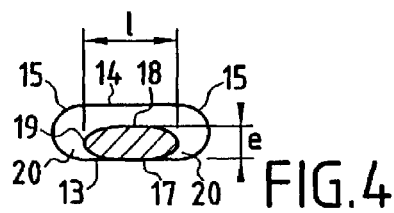
FIG. 4 is a cross-section view substantially on line IV—IV of FIG. 2.

In a construction particular to the invention, the bag 10 is associated with an elongate piece 16 constituted by a strap of flexible but non-stretchable material which also presents the feature of being placed inside the bag 10 so as to be connected to the inside face of one of its plane sides, e.g. the side 13 as shown in FIG. 4. Selecting an appropriate material to make the strap comes within the competence of the person skilled in the art.

The elongate piece 16 also presents the characteristic of presenting a right cross-section that is oblong in shape, of width l that is less than the width L of the bag 10, and that is preferably substantially equal to the width of one of the plane sides 13 or 14. According to another characteristic, the elongate piece 16 is of thickness e that is less than the distance between the plane sides 13 and 14, and the oblong section which is thus conferred on the strap is defined by two plane faces 17 and 18 which are interconnected by two convex edges 19.

The elongate piece 16 is connected via one of its faces, e.g. the face 17, to the inside surface of one of the plane sides of the bag 10, e.g. the side 13, such that the convex edges 15 and the edges 19 define between them kinds of half-crescents 20 extending from the plane side 13, whose function is described below.

In accordance with the invention, the above-described structure is obtained as a single piece, e.g. in the form of a one-piece molding.

The elongate piece 16 also presents another structural characteristic which is that of having a first end portion 21 which extends beyond the end 11 of the bag 10, being adjacent, at least in part, to the tube 8 so as to reinforce it. The elongate piece 16 also has a second end portion 22 which extends beyond the end 12 of the bag 10, said end being obtained, particularly when a practically one-piece manufacturing technique is used, by being bonded to the elongate piece 16 by adhesive.

Technical means are provided between the end portions 21 and 22 so as to enable them to be connected together with overlap so that the implant is then in the form of a closed band of regular structure that is practically circular and whose inner peripheral wall is occupied, as described below, by the bag 10.

In one embodiment, such connection means comprise notches 23 formed in the longitudinal edges of the first end portion 21, a slot 24 formed through the second portion 22, and at least one, and preferably two, D-loops 25 which are set back from the end portion 22, close thereto, while also being set back from the end 12 so as to project transversely from the outside face of the plane side 13. In the example shown, two D-loops 25 are provided, each having the particular feature of defining a kind of bridge of width substantially equal to that of the end portion 21 taken across the bottoms of the notches 23.

The structure of the implant of the invention is characterized by the gastric implant having a shape without any sharp outside edges that might injure the stomach wall because of the way the elongate piece 16 is located inside the bag 10. Furthermore, shaping the convex edges so as to leave half-crescents enables the bag to deform flexibly while it is being inflated without forming wrinkles or edges that could themselves injure the stomach wall.

Finally, as described below, the overlapping connection means between the end portions 21 and 22 hold these portions in a state that lies within the profile of the outer wall of the closed band, thus making it possible to reduce or even eliminate any risk of injuring the stomach wall.

The gastric implant is put into place as follows.

Figure 5:
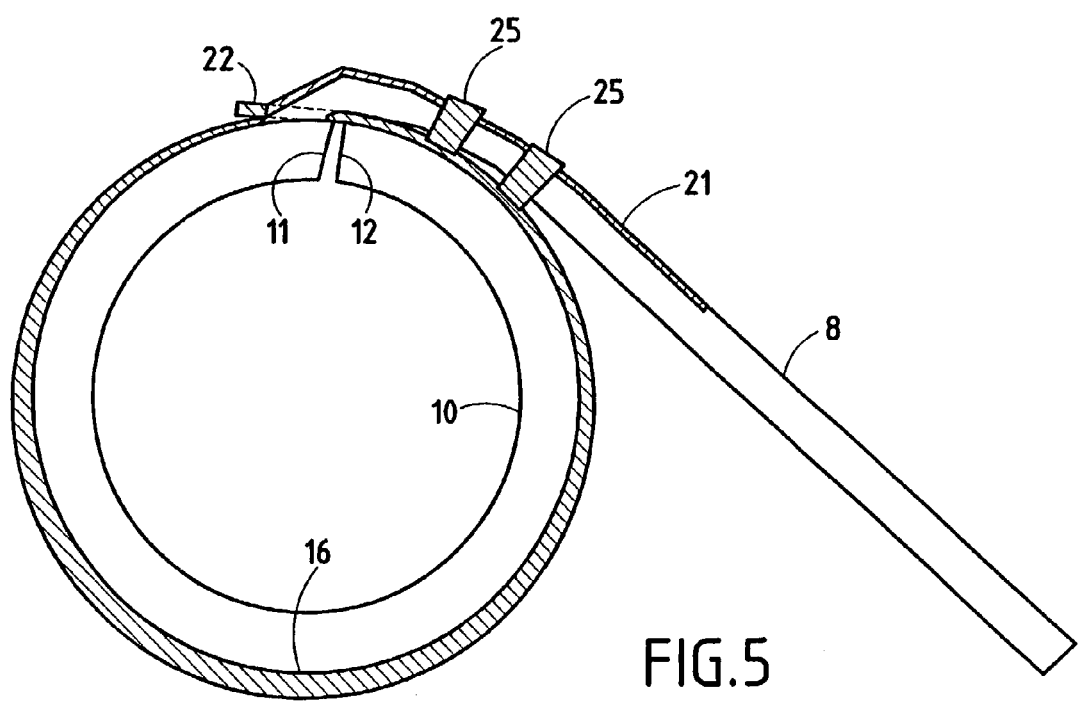
FIG. 5 is a plan view showing the subject matter of the invention in use.

With the bag 10 in the deflated state, the end portions 21 and 22 are directed towards each other so that the strap forms a band, a belt, a bracelet, or a hoop of substantially circular section, as shown in FIG. 5. This figure shows that the strap constituting the gastric implant is rolled up so that the inflatable bag 10 constitutes the inside surface of the band, with the elongate piece 16 being disposed towards its outer periphery.

In this situation, the overlapping connection means are implemented to engage the tube 8 and the first portion 21 through the slot 24 of the second end portion 22 so that the excess length of the end portion 21 can then be engaged through the D-loop(s) 25, thus achieving a connection that is firm, but that can be undone, by engaging the D-loops 25 in the notches 23.

In a preferred disposition it is advantageous, when there are two or more D-loops, for them to be spaced apart in the long direction of the gastric strap in a manner that corresponds to the spacing between two series of notches 23.

As a result, as shown in FIG. 5, the end portions 21 and 22 are connected together with one overlapping the other, thus making it possible firstly to eliminate any projecting and diverging end portions as are to be found in the prior art, and secondly to contribute to forming a closed band of section that approximates more closely to an ideal circular through section that is favorable for implantation on a stomach wall that is naturally relatively fragile.

Once the implant has been put into place, it suffices to engage the needle of a syringe in the box 6 through the membrane 7 and to inject a desired quantity of liquid such as physiological serum into the tube 8 and consequently into the inflatable bag 10 so as to inflate said bag and consequently reduce the through section of the band, which then applies a constriction effect on the stomach wall so as to calibrate the through channel between the sub-hiatal artificial pocket 3 and the main stomach pocket 4.

Figure 6:
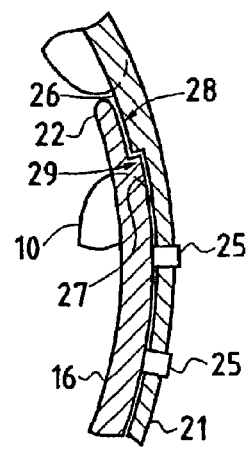
FIG. 6 is a section in elevation through a variant embodiment.

The overlapping connection means between the end portions 21 and 22 can be embodied in various ways, such as that shown in FIG. 6, for example. In such a variant, the first end portion 21, in its face 26 facing the face 27 of the second end portion 22 when they overlap, possesses a mutual-engagement shape 28 complementary to a receiving configuration 29 presented by the face 27.

The shape 28 is arranged in the zone of the end portion 21 close to the end 11 and upstream from the series of notches 23 relative to said end in such a manner as to enable said notches to co-operate with the D-loops 25 when said shape 28 is itself co-operating with the configuration 29.

Using the above-described means, any risk of aggression, damage, or puncturing due to sharp edges contacting the stomach wall is eliminated to a very great extent, or even completely. Furthermore, when the strap constituting the gastric implant is closed, it forms a band of section that is regular, making it possible to control accurately the through passage presented by the communicating channel between the sub-hiatal artificial pocket 3 and the main stomach pocket 4.

Figure 7:
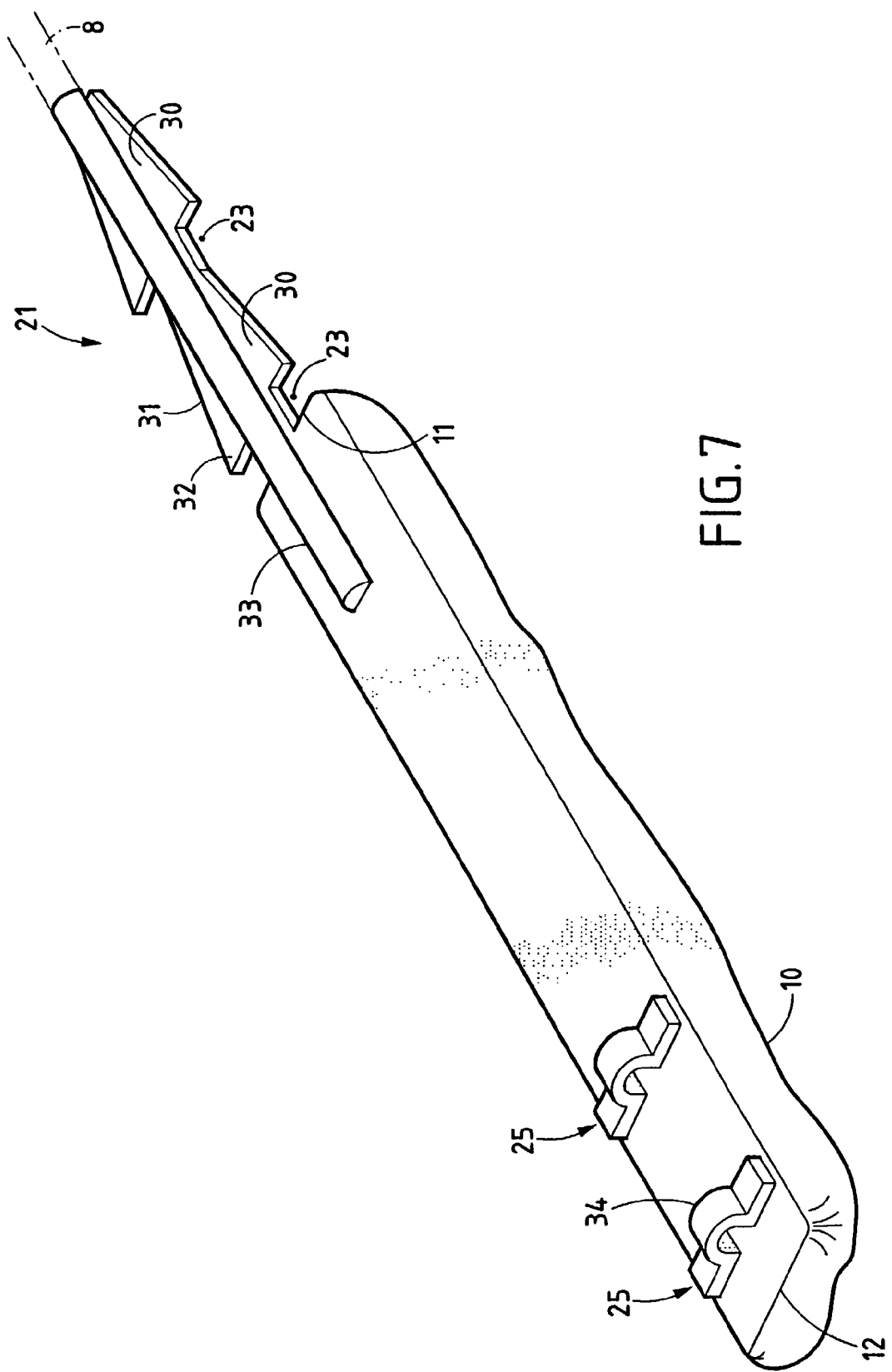
FIG. 7 is a perspective view showing another variant embodiment.

FIG. 7 shows another variant embodiment of the overlapping connection means. In this variant, the end portion 21 is provided with one or two spearhead shapes, each spearhead such as 30 presenting two sloping engagement ramps 31 terminating at two shoulders 32 which define, so to speak, the notches 23. This shape facilitates engagement in one or more D-loops 25 while subsequently ensuring that connection is firm and suitable for withstanding the traction stress induced by inflating the bag 10.

The portion 21 is also shaped by a duct 33 for connecting or extending the tube 8 for which a complementary shape 34 is provided in the D-loops 25. Such an embodiment makes it possible to eliminate the end portion 22.

INDUSTRIAL APPLICATION

An advantageous application for the invention lies in making adjustable gastric implants for combating obesity.

The invention is not limited to the examples described and shown since various modifications can be made thereto without going beyond its limit.

What is claimed is:

1. A gastric implant comprising a strap of material that is flexible but not stretchable associated with a tubular bag (10) of deformable flexible material that is closed at one end (12) and that communicates via its other end with a tube (8) connected to a box (6) having a self-sealing membrane (7) that can be pierced by a needle for injecting and/or removing a fluid so as to control, at will, the extent to which the bag is filled, said strap being provided with end portions enabling the strap to be looped in the form of a closed band whose inner peripheral surface is occupied by the bag, wherein:

the strap comprises an elongate piece (16) secured to the inside of the bag (10) which is shaped to present a right cross-section that is oblong, being defined by two substantially parallel plane sides (13–14) interconnected by two convex edges (15), the piece (16) having a right cross-section that is likewise oblong, with the greatest width thereof being substantially equal to the width of one of the plane sides (13–14);

the piece possesses convex longitudinal edges (19); and complementary overlapping connection means are provided between the end portions of the strap.

2. A gastric implant according to claim 1, wherein the piece (16), the bag (10), the overlapping connection means, and the tube (8) are made in substantially one-piece manner.

3. A gastric implant according to claim 1, wherein the piece (16), the bag (10), the overlapping connection means, and the tube (8) are made by molding.

4. A gastric implant according to claim 1, wherein the piece (16) is defined by two plane faces (17 and 18) and by two rounded edges (19) and said piece is connected to the inside of the bag via one of its plane faces which is coplanar with the inside face of one of the plane sides of the bag.

5. A gastric implant according to claim 1, wherein the piece (16) has two end portions (21–22) extending beyond the bag, with a first end portion being connected to the tube (8), and the overlapping connection means between said end portions comprises at least one series of notches (23) presented by said first portion and a series of D-loops (25) provided set back from the end of the strap opposite to the first end portion.

6. A gastric implant according to claim 5, wherein the overlapping connection means comprises, on a face of the first end portion, an engagement shape (28) formed close to a connection zone between the first end portion and the bag, and on a facing face of the second end portion (22), a complementary shape (29).

7. A gastric implant according to claim 1, wherein the overlapping connection means comprise solely an end portion (21) provided with at least one series of notches (23) and extending from the other end, together with D-loops (25) provided set back from the closed end of said bag.

8. A gastric implant according to claim 7, wherein the end portion (21) provided with the at least one series of notches presents a shape with two spearhead pieces, defining a duct (33) corresponding to the tube (8), and the D-loops (25) are of a shape (34) that is complementary to said duct.

* * * * *